US008792697B2

(12) United States Patent
Tomoto

(10) Patent No.: US 8,792,697 B2
(45) Date of Patent: Jul. 29, 2014

(54) IMAGE PROCESSING APPARATUS AND IMAGE PROCESSING METHOD

(71) Applicant: Olympus Medical Systems Corp., Tokyo (JP)

(72) Inventor: Yusuke Tomoto, Hino (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 14/074,268

(22) Filed: Nov. 7, 2013

(65) Prior Publication Data

US 2014/0093155 A1 Apr. 3, 2014

Related U.S. Application Data

(63) Continuation of application No. PCT/JP2012/062299, filed on May 14, 2012.

(30) Foreign Application Priority Data

Sep. 8, 2011 (JP) .................................. 2011-196256

(51) Int. Cl.
*G06K 9/00* (2006.01)
*A61B 5/00* (2006.01)
(52) U.S. Cl.
CPC .................... *A61B 5/0033* (2013.01)
USPC .......................................................... 382/128
(58) Field of Classification Search
None
See application file for complete search history.

(56) References Cited

U.S. PATENT DOCUMENTS

2011/0085717 A1* 4/2011 Matsuda ........................ 382/128

FOREIGN PATENT DOCUMENTS

| EP | 2 305 091 A1 | 4/2011 | |
|---|---|---|---|
| JP | 2005-157902 A | 6/2005 | |
| JP | 2009-297450 A | 12/2009 | |
| JP | 2010-184057 | * 8/2010 | ............... A61B 1/04 |
| JP | 2010-184057 A | 8/2010 | |
| WO | WO 2009/154125 A1 | 12/2009 | |

OTHER PUBLICATIONS

International Search Report dated Aug. 14, 2012 issued in PCT/JP2012/062299.

* cited by examiner

*Primary Examiner* — Amara Abdi
(74) *Attorney, Agent, or Firm* — Scully, Scott, Murphy & Presser, P.C.

(57) ABSTRACT

An image processing apparatus includes: a basic shape matching section that extracts, as a structure region, a predetermined structural object included in an image obtained by picking up an image of a mucosal surface of a living body, and matches each of regions resulting from the structure region being divided, the regions each including at least one pixel, with a first region having a first basic shape or a second region having a second basic shape; a feature value calculating section that sequentially sets regions of interest from among the regions matched by the basic shape matching section, and calculates counts of the first regions and the second regions adjacent to each of the regions of interest; and a classification section that classifies the structure region based on a result of the calculation by the feature value calculating section.

12 Claims, 5 Drawing Sheets

• CIRCLE
○ LINE

⊖ STRAIGHT LINE
● CIRCLE
⊛ CURVE
⫿ DIVARICATION

ADJACENT PIXELS

|  |  | CIRCLE | STRAIGHT LINE | DIVARICATION | CURVE |
|---|---|---|---|---|---|
| PIXEL OF INTEREST | CIRCLE | 0 | 0 | 0 | 0 |
|  | STRAIGHT LINE | 0 | 124 | 10 | 30 |
|  | DIVARICATION | 0 | 10 | 39 | 23 |
|  | CURVE | 0 | 30 | 23 | 73 |

ADJACENT REGIONS

|  |  | CIRCLE | STRAIGHT LINE | DIVARICATION | CURVE |
|---|---|---|---|---|---|
| REGION OF INTEREST | CIRCLE | 0 | 0 | 0 | 0 |
|  | STRAIGHT LINE | 0 | 0 | 3 | 2 |
|  | DIVARICATION | 0 | 3 | 0 | 0 |
|  | CURVE | 0 | 2 | 0 | 0 |

IMAGE PROCESSING APPARATUS AND IMAGE PROCESSING METHOD

CROSS REFERENCE TO RELATED APPLICATION

This application is a continuation application of PCT/JP2012/062299 filed on May 14, 2012 and claims benefit of Japanese Application No. 2011-196256 filed in Japan on Sep. 8, 2011, the entire contents of which are incorporated herein by this reference.

BACKGROUND OF THE INVENTION

1. Field of the Invention

The present invention relates to an image processing apparatus and an image processing method, and specifically relates to an image processing apparatus and an image processing method used for, e.g., diagnosis of a living tissue.

2. Description of the Related Art

In recent years, diagnostic approaches using patterns of blood vessels under a mucous membrane and/or patterns of microstructures in a mucosal surface included in a medical image, such as an image of the inside of a lumen, picked up by inserting an endoscope into a body cavity of a subject have been proposed.

Also, in recent years, as an example of techniques for enabling the aforementioned diagnostic approaches to be aided by, e.g., computers, image processing for extracting and quantifying, e.g., patterns of shapes of blood vessels under a mucous membrane of a living body and/or patterns of microstructures in a mucosal surface of a living body included in a medical image have been proposed.

For example, Japanese Patent Application Laid-Open Publication No. 2005-157902 discloses an image analysis method in which image data of an original image designated by operation of an operating apparatus and the obtained image data of the original image is processed to generate a binarized image, a labeled image, a line-thinned image, a blood vessel shape feature value, a blood vessel feature value, and an image subjected to analysis processing.

SUMMARY OF THE INVENTION

An image processing apparatus according to an aspect of the present invention includes: a basic shape matching section that extracts, as a structure region, a predetermined structural object in an image obtained by picking up an image of a mucosal surface of a living body, the image including at least one pixel, and matches each of regions resulting from the structure region being divided, the regions each including at least one pixel, with a first region having a first basic shape or a second region having a second basic shape that is different from the first basic shape; a feature value calculating section that sequentially sets regions of interest from among the regions matched by the basic shape matching section, and calculates counts of the first regions and the second regions adjacent to each of the sequentially set regions of interest; and a classification section that classifies the structure region based on a result of the calculation by the feature value calculating section.

A method for operation of an image processing apparatus according to an aspect of the present invention includes: a basic shape matching step of a basic shape matching section extracting, as a structure region, a predetermined structural object in an image obtained by picking up an image of a mucosal surface of a living body, the image including at least one pixel, and matching each of regions resulting from the structure region being divided, the regions each including at least one pixel, with a first region having a first basic shape or a second region having a second basic shape that is different from the first basic shape; a feature value calculating step of a feature value calculating section setting regions of interest from among the regions matched in the basic shape matching step, and calculating counts of the first regions and the second regions adjacent to each of the set regions of interest; and a classification step of a classification section classifying the structure region based on a result of the calculation in the feature value calculating step.

DETAILED DESCRIPTION OF THE PREFERRED EMBODIMENTS

An embodiment of the present invention will be described with reference to the drawings.

FIGS. 1 to 10 relates to an embodiment of the present invention.

Figure 1:
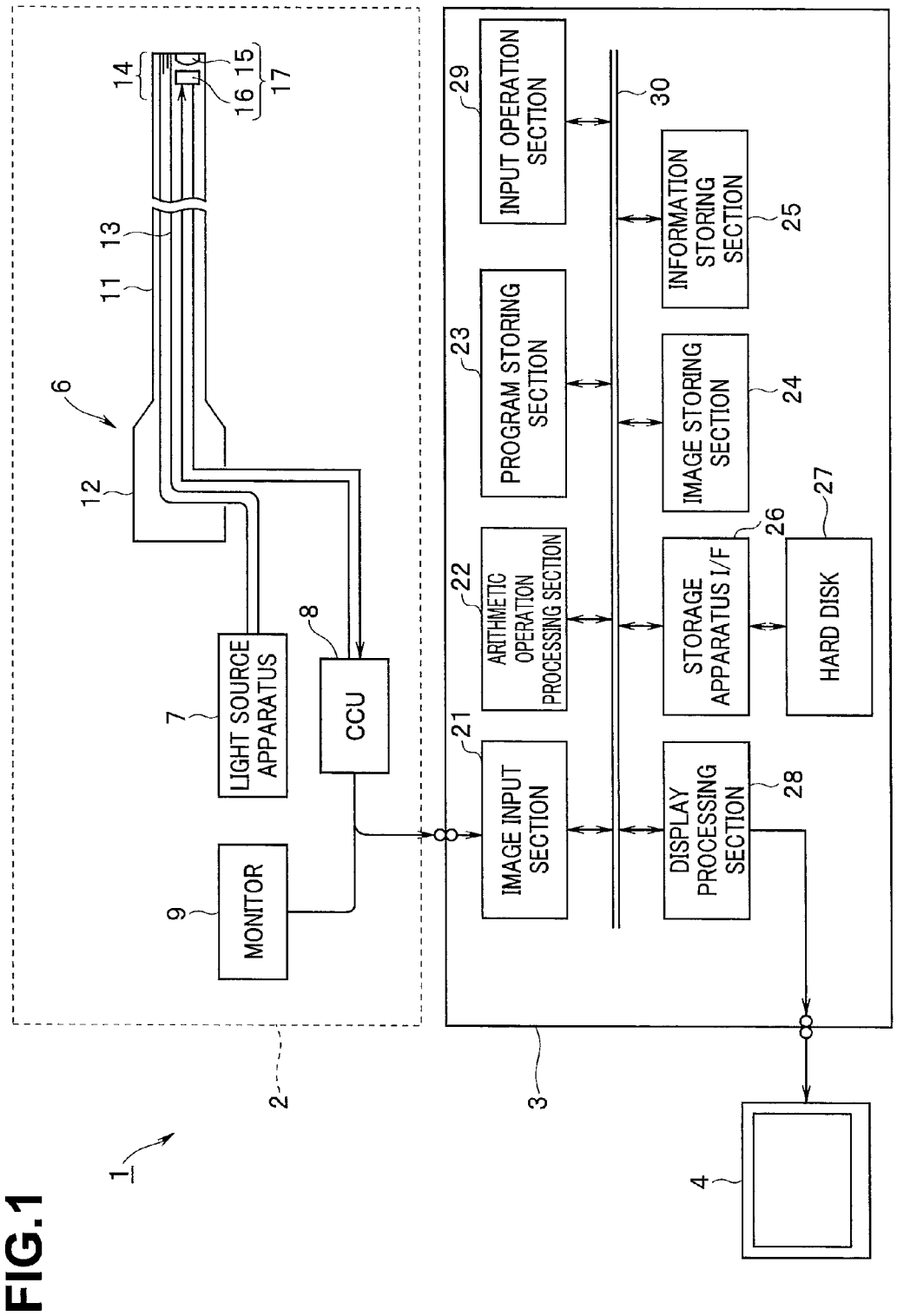
FIG. 1 is a diagram illustrating a configuration of a main part of a medical system including an image processing apparatus according to an embodiment of the present invention.

FIG. 1 is a diagram illustrating a configuration of a main part of a medical system including an image processing apparatus according to an embodiment of the present invention.

As illustrated in FIG. 1, a medical system 1 includes: a medical observation apparatus 2 that picks up an image of an object such as a mucosal surface of a living body inside a body cavity to output a video signal; an image processing apparatus 3 including, e.g., a personal computer, the image processing apparatus 3 performing image processing on the video signal outputted from the medical observation apparatus 2 and outputting the video signal subjected to the image processing as an image signal; and a monitor 4 that displays an image based on the image single outputted from the image processing apparatus 3.

Also, the medical observation apparatus 2 includes: an endoscope 6 that, upon the endoscope 6 being inserted into a body cavity, picks up an image of an object inside the body cavity to output a picked-up image signal; a light source apparatus 7 that supplies illuminating light (for example, RGB light) for illuminating the object, an image of which is picked up by the endoscope 6; a camera control unit (hereinafter abbreviated as "CCU") 8 that performs various types of control on the endoscope 6 and performs signal processing on the picked-up image signal outputted from the endoscope 6 to generate and output a video signal; and a monitor 9 that displays the image of the object picked up by the endoscope 6 based on the video signal outputted from the CCU 8.

The endoscope 6, which serves as a medical image pickup apparatus, includes an insertion portion 11 to be inserted into a body cavity, and an operation portion 12 provided on the proximal end side of the insertion portion 11. Also, a light guide 13 for conveying illuminating light supplied from the light source apparatus 7 is inserted through the inside of the insertion portion 11 from the proximal end side to a distal end portion 14 on the distal end side.

The light guide 13 is configured so that the distal end side thereof is arranged in the distal end portion 14 of the endoscope 6 and the rear end side thereof is connectable to the light source apparatus 7. Then, such configuration allows illuminating light supplied from the light source apparatus 7 to be conveyed by the light guide 13 and then exit from an illumination window (not illustrated) provided at a distal end face of the distal end portion 14 of the insertion portion 11. Then, e.g., a living tissue as an object is illuminated with the illuminating light exiting from the illumination window.

In the distal end portion 14 of the endoscope 6, an image pickup section 17 including an objective optical system 15 attached to an observation window (not illustrated) arranged at a position adjacent to the illumination window, and an image pickup device 16, which includes, e.g., a CCD, arranged at a position where an image through the objective optical system 15 is formed are provided.

The image pickup device 16 is connected to the CCU 8 via signal wires. The image pickup device 16 is driven based on a drive signal outputted from the CCU 8, and outputs a picked-up image signal obtained by picking up an image of an object formed through the objective optical system 15 to the CCU 8.

The picked-up image signal inputted to the CCU 8 is subjected to signal processing in a signal processing circuit (not illustrated) provided inside the CCU 8 and thereby converted into a video signal and the video signal is outputted. Then, the video signal outputted from the CCU 8 is inputted to the monitor 9 and the image processing apparatus 3. Consequently, an image of the object based on the video signal outputted from the CCU 8 is displayed on the monitor 9.

The image processing apparatus 3 includes: an image input section 21 that subjects the video signal outputted from the medical observation apparatus 2 to processing such as A/D conversion to generate image data; an arithmetic operation processing section 22 including, e.g., a CPU, the arithmetic operation processing section 22 performing various types of processing on, e.g., the image data outputted from the image input section 21; a program storing section 23 that stores, e.g., programs (and software) for the processing performed in the arithmetic operation processing section 22; an image storing section 24 capable of storing, e.g., the image data outputted from the image input section 21; and an information storing section 25 capable of storing a result of the processing in the arithmetic operation processing section 22.

Also, the image processing apparatus 3 includes: a storage apparatus I/F (interface) 26 connected to a data bus 30, which will be described later; a hard disk 27 capable of storing the result in the arithmetic operation processing section 22, the processing result being outputted via the storage apparatus interface 26; a display processing section 28 that generates and outputs an image signal for displaying an image of, e.g., the result of the processing in the arithmetic operation processing section 22 on the monitor 4; and an input operation section 29 including, e.g., an input apparatus such as a keyboard, the input operation section 29 allowing input of, e.g., parameters for the processing in the arithmetic operation processing section 22 and instructions for operation of the image processing apparatus 3.

Note that the image input section 21, the arithmetic operation processing section 22, the program storing section 23, the image storing section 24, the information storing section 25, the storage apparatus interface 26, the display processing section 28 and the input operation section 29 in the image processing apparatus 3 are interconnected via the data bus 30.

Figure 2:
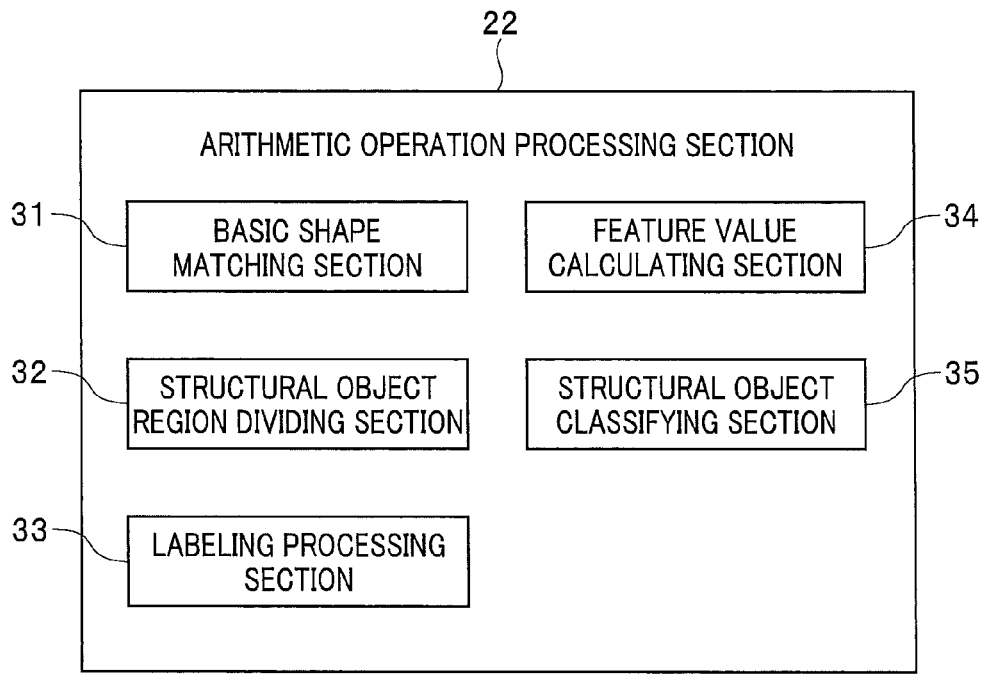
FIG. 2 is a diagram illustrating main processing functions of an arithmetic operation processing section according to the present embodiment.

FIG. 2 is a diagram illustrating main processing functions of the arithmetic operation processing section according to the present embodiment.

As illustrated in FIG. 2, the arithmetic operation processing section 22 has a processing function as a basic shape matching section 31, a processing function as a structural object region dividing section 32, a processing function as a labeling processing section 33, a processing function as a feature value calculating section 34 and a processing function as a structural object classifying section 35.

The basic shape matching section 31 calculates a predetermined feature value of each pixel or each region in image data outputted from the image input section 21, extracts an arbitrary structural object included in the image data as a structure region, and performs processing for matching each pixel or each region in the extracted structure region with any of plural types of predetermined basic shapes based on a result of the calculation of the predetermined feature value. Note that details of such processing in the basic shape matching section 31 will be described later.

The structural object region dividing section 32 performs processing for dividing (the structural object as) the structure region subjected to matching with the plural types of predetermined basic shapes by means of the processing in the basic shape matching section 31, into regions according to the respective basic shapes, based on a result of the processing in the basic shape matching section 31.

The labeling processing section 33 performs processing for labeling each of the structural objects resulting from the region division by the structural object region dividing section 32, based on a result of the processing in the structural object region dividing section 32.

The feature value calculating section 34 calculates a feature value representing a feature of each of the structural objects labeled by the labeling processing section 33, based on a result of the processing in the labeling processing section 33. Note that details of such processing in the feature value calculating section 34 will be described later.

The structural object classifying section 35 performs processing for classifying the respective structural objects labeled by the labeling processing section 33 into respective specific structural objects relating to a living tissue such as blood vessels and microstructures of a mucous membrane, based on results of the processing in the labeling processing section 33 and the feature value calculating section 34. Note that details of such processing in the structural object classifying section 35 will be described later.

Figure 3:
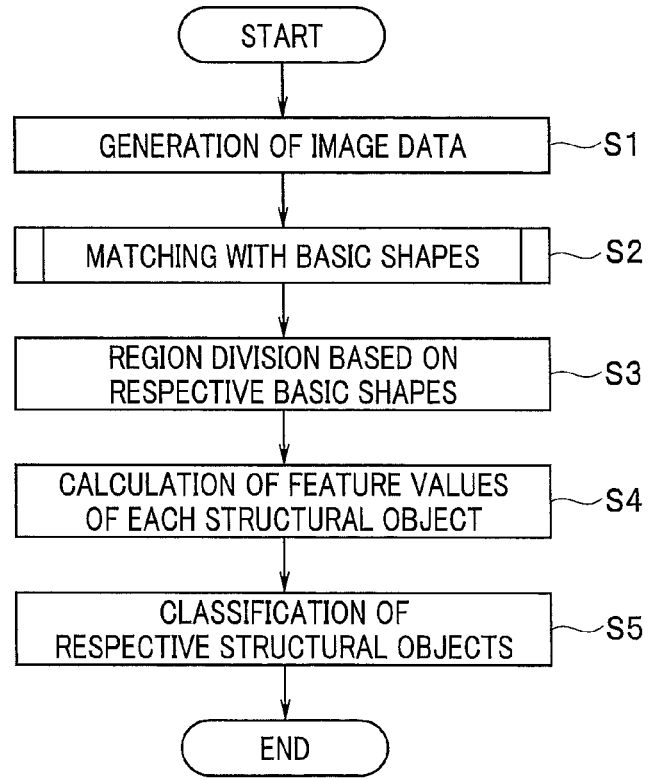
FIG. 3 is a flowchart illustrating an example of processing, etc., performed by the image processing apparatus according to the present embodiment.

Next, processing, etc., performed in the image processing apparatus 3 in the medical system 1 according to the present embodiment will be described mainly with reference to the flowchart in FIG. 3. FIG. 3 is a flowchart illustrating an example of processing, etc., performed by the image processing apparatus according to the present embodiment.

First, a user turns on a power supply to the respective parts of the medical system 1 and then, inserts the insertion portion 11 until, for example, the distal end portion 14 reaches a desired observation site inside a body cavity of a subject. Consequently, an object including a living body mucosal surface is illuminated by illuminating light (RGB light) exiting from the distal end portion 14, and an image of the object is picked up by the image pickup section 17 and a picked-up image signal according to the picked-up image of the object is outputted to the CCU 8.

The CCU 8 performs signal processing on the picked-up image signal outputted from the image pickup device 16 in the image pickup section 17, via the signal processing circuit (not illustrated) to convert the picked-up image signal into a video signal, and outputs the video signal to the medical image processing apparatus 3 and the monitor 9. Then, the monitor 9 displays the image of the object picked up by the image pickup section 17, based on the video signal outputted from the CCU 8.

The image input section 21 performs processing, such as A/D conversion, on the video signal inputted from the medical observation apparatus 2 to generate image data (step S1 in FIG. 3) and outputs the generated image data to the arithmetic operation processing section 22 (and the image storing section 24).

Subsequently, the basic shape matching section 31 in the arithmetic operation processing section 22 performs processing for calculating a predetermined feature value of each pixel or each region in the image data outputted from the image input section 21, extracting an arbitrary structural object in the image data as a structure region, and matching each pixel or each region in the extracted structure region with any of plural types of predetermined basic shapes based on a result of the calculation of the predetermined feature values (step S2 in FIG. 3).

Figure 4:
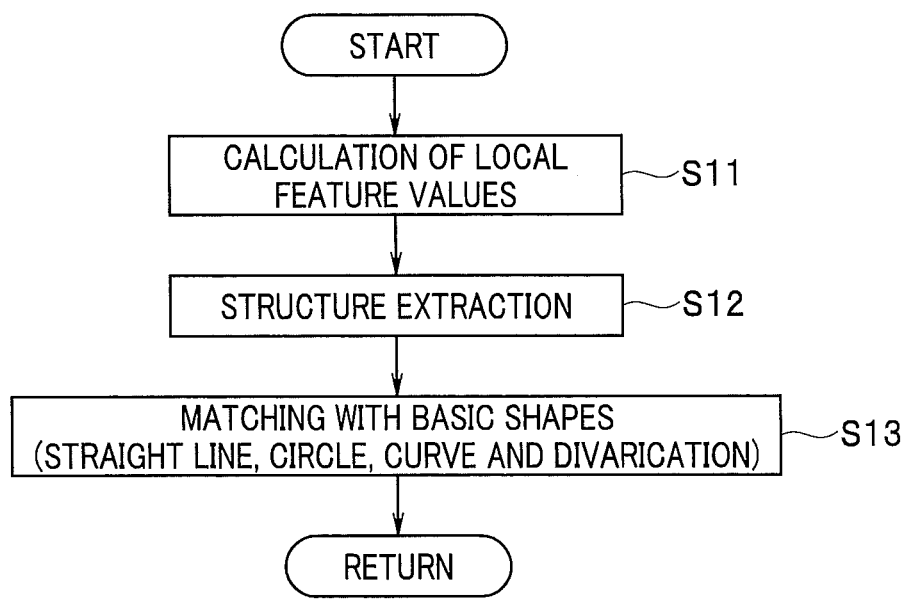
FIG. 4 is a flowchart illustrating an example of processing, etc., for basic shape matching.
Figure 5:
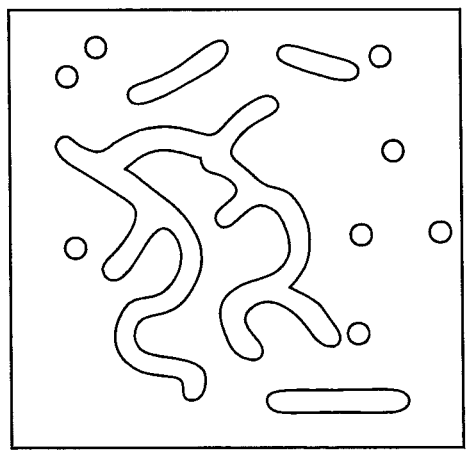
FIG. 5 is a diagram illustrating an example of an image region included in image data to be processed.

Here, details of the processing, etc., performed in step S2 in FIG. 3 will be described mainly with reference to the flowchart in FIG. 4. Note that for simplicity, the below description is provided assuming that an image region such as illustrated in FIG. 5 is included in at least a part of the image data generated by the image input section 21 based on the video signal inputted to the image processing apparatus 3. FIG. 4 is a flowchart illustrating an example of processing, etc., for matching with the basic shapes. FIG. 5 is a diagram illustrating an example of an image region included in image data to be processed.

The basic shape matching section 31 in the arithmetic operation processing section 22 calculates local feature values of the image data generated by the image input section 21 (step S11 in FIG. 4).

More specifically, while the basic shape matching section 31, for example, sequentially sets all the pixels included in the image data generated by the image input section 21 one by one from the upper left pixel to the lower right pixel, as pixels of interest, the basic shape matching section 31 sequentially calculates feature values of the set pixels of interest.

Note that the basic shape matching section 31 is not limited to one that sequentially sets pixels of interest that each include one pixel and calculates feature values of the respective pixels of interest in step S11 in FIG. 4, and may be, for example, one that sequentially sets regions of interest that each include a plurality of pixels and calculates feature values of the respective set regions of interest.

Also, the basic shape matching section 31 calculates, for example, a feature value AC1 relating to a direction of a local change (in luminance value or pixel value) of each pixels of interest, a feature value AC2 relating to a magnitude of the local change, and a shape feature value AC3 based on the direction and the magnitude of the change, as the aforementioned local feature values.

More specifically, the basic shape matching section 31 calculates a 2×2 Hessian matrix corresponding to second-order partial derivatives according to horizontal and vertical positions for a luminance value of each pixel to obtain eigenvalues $\lambda1$ and $\lambda2$ ($\lambda1 \leq \lambda2$) and eigenvectors e1 and e2 corresponding to the eigenvalues $\lambda1$ and $\lambda2$. Note that the eigenvectors e1 and e2 correspond to the feature value AC1, and the eigenvalues $\lambda1$ and $\lambda2$ correspond to the feature value AC2.

Furthermore, the basic shape matching section 31 performs an arithmetic operation using the feature value AC2 obtained in the above arithmetic operation to calculate a value of a linearity degree LD representing a degree of a linear shape characteristic of each pixels of interest and a value of a circularity degree CD representing a degree of a circular shape characteristic of the pixels of interest, respectively, as the shape feature value AC3.

More specifically, the basic shape matching section 31 performs an arithmetic operation of $(\lambda2-\lambda1)/\lambda2$ to obtain the value of the linearity degree LD. Also, the basic shape matching section 31 performs an arithmetic operation of $\lambda1/\lambda2$ to obtain the value of the circularity degree CD.

Figure 6:
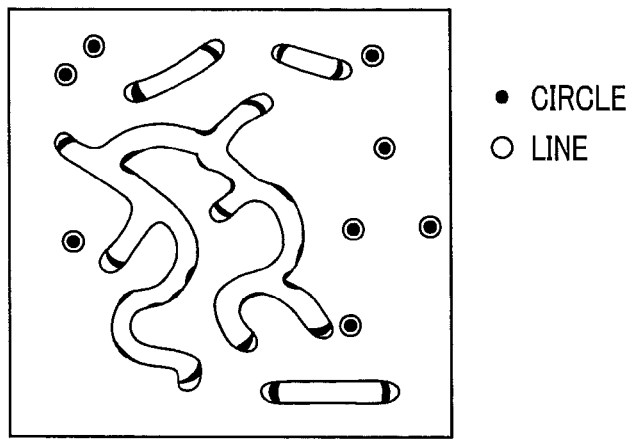
FIG. 6 is a diagram illustrating an example of results of calculation of shape feature values in the image region in FIG. 5.

Then, the basic shape matching section 31 obtains, for example, results of the calculation of the shape feature values AC3 as illustrated in FIG. 6 for the image region illustrated in FIG. 5, based on the respective values obtained as the linearity degree LD and the circularity degree CD. FIG. 6 is a diagram illustrating an example of results of calculation of shape feature values in the image region in FIG. 5.

According to the results of calculation of the shape feature values AC3 illustrated in FIG. 6, parts with a large value of the linearity degree LD (each indicated as a line in FIG. 6) and parts with a large value of the circularity degree CD (each indicated as a circle in FIG. 6) in the image region illustrated in FIG. 5 can be extracted, respectively.

Note that the basic shape matching section 31 may be one that calculates a gradient direction of each pixels of interest as the feature value AC1. Also, the basic shape matching section 31 may be one that calculates a gradient magnitude of each pixels of interest as the feature value AC2. Furthermore, the basic shape matching section 31 may be one that calculates a value of a shape index of each pixels of interest as the feature value AC3.

Also, the basic shape matching section 31 extracts an arbitrary structural object included in the image data outputted from the image input section 21, based on a result of the processing in step S11 in FIG. 4 as a structure region (step S12 in FIG. 4).

More specifically, the basic shape matching section 31 extracts, for example, a pixel meeting any of conditions that the feature value AC2 is equal to or below a certain threshold value T1high, the feature value AC2 is equal to or exceeds a certain threshold value T1low (however, T1high>T1low), the feature value AC3 is equal to or below a certain threshold value T2high and the feature value AC3 is equal to or exceeds a certain threshold value T2low (however, T2high>T2low), as a pixel included in a structure region that is a structural object (to be extracted).

Note that the respective pieces of information of the threshold values T1high, T1low, T2high and T2low are stored in advance in, for example, the information storing section 25. Then, the basic shape matching section 31 performs processing using the respective pieces of information of the threshold values T1high, T1low, T2high and T2low stored in advance in the information storing section 25, in step S12 in FIG. 4.

The basic shape matching section 31 performs processing for matching each pixel or each region in the structure region extracted in step S12 in FIG. 4 with any of the plural types of predetermined basic shapes, based on results of calculation of the respective feature values in step S11 in FIG. 4 (step S13 in FIG. 4), and subsequently performs the processing in step S3 in FIG. 3.

Note that in the present embodiment, as the plural types of predetermined basic shapes, for example, four types of basic shapes: circle, straight line, curve and divarication, which are minute unit partial shapes included in a structural object in a mucosal surface of a living body are set in advance. Then, if the four types of basic shapes are set in advance, the basic shape matching section 31 performs the following determination processing based on the results of the calculation of the respective feature values in step S12 in FIG. 4 to perform processing for matching each pixel or each region in the structure region extracted in step S12 in FIG. 4 with any one of the respective basic shapes.

More specifically, the basic shape matching section 31 matches each pixel or each region for which the determination result that the value of the linearity degree LD is large compared to the value of the circularity degree CD and directions of the pixel or the region concentrate on one certain direction has been obtained, with a straight line.

Also, the basic shape matching section 31 matches each pixel or each region for which the determination result that the value of the linearity degree LD is large compared to the value of the circularity degree CD and directions of the pixel or the region concentrate on two different directions has been obtained, with a curve.

Also, the basic shape matching section 31 matches each pixel or each region for which the determination result that the value of the circularity degree CD is large compared to the value of the linearity degree LD and directions of the pixel or the region disperse, with a circle.

Also, the basic shape matching section 31 matches each pixel or each region for which the determination result that the value of the linearity degree LD and the value of the circularity degree CD are substantially the same and directions from a pixel having a linearity degree LD disperse in several directions, with a divarication.

Note that the processing in step S13 in FIG. 4 in the present embodiment may be performed using, for example, shapes resulting from subdivision of the aforementioned four types of basic shapes according to characteristics such as thickness, dimensions and color.

The structural object region dividing section 32 performs processing for dividing (the structural object as) the structure region matched with the plural types of basic shapes, according to the respective basic shapes, based on a result of the processing by the basic shape matching section 31 in step S2 in FIG. 3 (result of the processing in step S13 in FIG. 4) (step S3 in FIG. 3).

Figure 7:
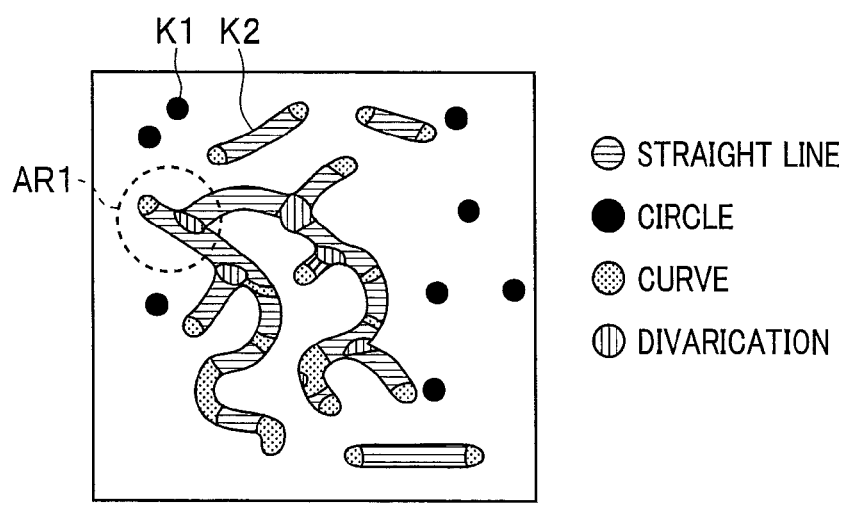
FIG. 7 is a diagram illustrating an example of a case where each structural object included in the image region in FIG. 5 is divided into regions based on respective basic shapes.

More specifically, for example, if the region division processing in step S3 in FIG. 3 is performed on the image data illustrated in FIG. 5 (and FIG. 6) where four types of basic shapes: circle, straight line, curve and divarication, are set in advance, a processing result such as illustrated in FIG. 7 can be obtained. FIG. 7 is a diagram illustrating an example of a case where the respective structural objects included in the image region in FIG. 5 are divided into regions based on the respective basic shapes.

The labeling processing section 33 performs processing for labeling each of the structural objects resulting from the region division by the structural object region dividing section 32, based on a result of the processing in step S3 in FIG. 3.

Subsequently, the feature value calculating section 34 calculates feature values of each structural object labeled by the labeling processing section 33, based on a result of the processing in the labeling processing section 33 (step S4 in FIG. 3).

Here, e.g., methods for calculating various feature values that can be calculated by the processing in step S4 in FIG. 3 will be described. Note that for simplicity, the below description is provided taking a case where four types of basic shapes: circle, straight line, curve and divarication, are set in advance, as an example.

First, specific methods for calculating a feature value FV1 according to a frequency of appearance of each basic shape in the result of the region division in step S3 in FIG. 3 will be described. Note that the feature value calculating section 34 in the present embodiment may use any of the below-described feature value FV1 calculation methods alone or a plurality of the methods in combination.

The feature value calculating section 34 calculates a frequency of appearance of pixels matched with each of the four types of basic shapes where all pixels included in one structural object is 100%, as the feature value FV1.

More specifically, for example, for the structural object K1 in FIG. 7, a feature value FV1 calculation result that the circle basic shape=100%, the straight line basic shape=0%, the curve basic shape=0% and the divarication basic shape is =0% can be obtained. Note that the feature value calculating section 34 in the present embodiment may calculate a feature value FV1 by multiplying the frequency of appearance of the pixels matched with each basic shape such as described above, by any of values of a width, a length or an area of the structural object.

The feature value calculating section 34 calculates the respective counts of pixels corresponding to the four types of basic shapes in one structural object, as the feature value FV1.

The feature value calculating section 34 calculates the respective counts of regions resulting from one structural object being divided based on the four types of basic shapes, as the feature value FV1.

More specifically, for example, for the structural object K2 in FIG. 7, a feature value FV1 calculation result that the circle region count=0, the straight line region count=1, the curve region count=2 and the divarication region count=0 can be obtained.

Note that the above-described feature value FV1 calculation methods can be employed in a substantially same manner whether a part or all of image regions in one image data is subject to the calculation.

Also, the feature value calculating section 34 in the present embodiment may determine an average value and/or a statistic value of, e.g., dispersion calculated based on the frequency of appearance of each basic shape, as a feature value FV1.

Also, the feature value calculating section 34 in the present embodiment calculates a feature value FV1 for a particular type of basic shape selected from the respective basic shapes.

Also, the feature value calculating section 34 in the present embodiment may determine, for example, a result of a product-sum operation to add up respective values obtained by multiplying the frequencies of appearance of the respective basic shapes by respective weight coefficients, as a feature value FV1.

Next, specific methods for calculating a feature value FV2 according to positional relationship among basic shapes of one or more types in the result of the region division in step S3 in FIG. 3 will be described. Note that the feature value calculating section 34 in the present embodiment may use any of the below-described feature value FV2 calculation methods alone or a plurality of the methods in combination.

Where P types of basic shapes are set in advance, the feature value calculating section 34 scans each region subsequent to region division included in one structural object, and puts an adjacency relationship (connection relationship) among the respective basic shape regions obtained based on a result of the scan into a p-adic number code to calculate a feature value FV2.

More specifically, for example, where the four types of basic shapes are set in advance, each structural object labeled by the labeling processing section 33 is put into a quaternary number code including circle=0, straight line=1, divarication=2 and curve=3. Then, the feature value calculating section 34 scans, for example, the structural object K2 in FIG. 7 from the left side to the right side of the image data and puts a result of the scan into a quaternary number code such as mentioned above to obtain a feature value FV2 calculation result of "313".

The feature value calculating section 34 analyzes each pixel subsequent to region division included in one structural object and puts adjacency relationships (connection relationships) among pixels of the respective basic shapes obtained based on a result of the analysis into a matrix to calculate a feature value FV2.

Figures 8, 9, 10:
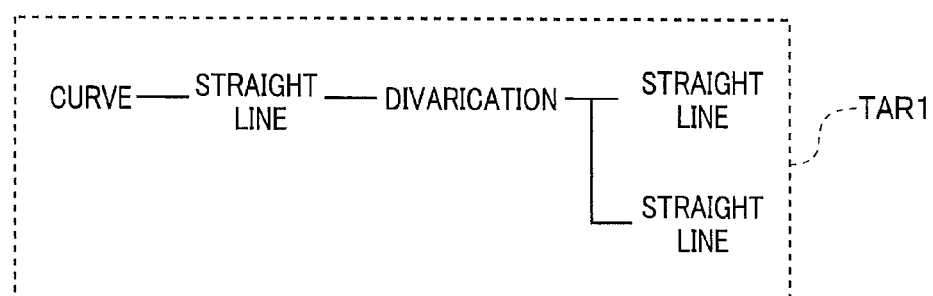
FIG. 8 is a diagram illustrating an example of a matrix representing counts of pixels of respective basic shapes adjacent to a pixel of interest relative to respective basic shapes matched with the pixel of interest.
FIG. 9 is a diagram illustrating an example of a matrix representing counts of regions of respective basic shapes adjacent to a region of interest relative to respective basic shapes matched with the region of interest.
FIG. 10 is a diagram illustrating an example of a case where basic shapes included in the region AR1 in FIG. 7 are represented in the form of a tree structure.

FIG. 8 is a diagram illustrating an example of a matrix representing counts of pixels of respective basic shapes adjacent to a pixel of interest relative to respective basic shapes matched with the pixel of interest.

More specifically, the feature value calculating section 34 sequentially sets pixels of interest one by one from respective pixels subsequent to region division included in one structural object, and counts, by basic shape, basic shapes matched with respective pixels adjacent to each set pixels of interest, which are located at four or eight adjacent positions, to obtain a matrix, for example, as illustrated in FIG. 8, representing counts of pixels of the respective basic shapes adjacent to pixels of interest relative to the respective shapes matched with the pixels of interest, as a feature value FV2. (In other words, in the structural object indicated by the matrix in FIG. 8, for pixels of interest matched with the straight line basic shape, there are 124 adjacent pixels matched with the straight line basic shape).

The feature value calculating section 34 analyzes each region subsequent to region division included in one structural object and puts adjacency relationships (connection relationships) among the regions of the respective basic shapes as a result of the analysis into a matrix to calculate a feature value FV2.

FIG. 9 is a diagram illustrating an example of a matrix representing counts of regions of respective basic shapes adjacent to a region of interest relative to respective basic shapes matched with the region of interest.

More specifically, the feature value calculating section 34 sequentially sets regions of interest one by one from respective regions subsequent to region division included in one structural object and counts, by basic shape, basic shapes matched with respective regions adjacent to each set region of interest to obtain a matrix, for example, as illustrated in FIG. 9, representing counts of regions of the respective basic shapes adjacent to the regions of interest relative to the respective basic shapes matched with the regions of interest, as a feature value FV2. (In other words, in the structural object indicated by the matrix in FIG. 9, for regions of interest matched with the divarication basic shape, there are three adjacent regions matched with the straight line basic shapes).

The feature value calculating section 34 analyzes each region subsequent to from region division included in one structural object or a plurality of structural objects and calculates a distribution interval between basic shapes of one or more types obtained based on a result of the analysis, as a feature value FV2.

More specifically, the feature value calculating section 34 calculates, for example, a distance between regions matched with the divarication basic shape from among the four types of basic shapes, as a feature value FV2. Then, the feature value FV2 calculated as described above enables, for example, existence or non-existence of a high-grade lesion to be quantitatively determined according to a magnitude of the value of the feature value FV2.

Also, the feature value calculating section 34 calculates, for example, a distance between regions matched with the circle basic shape from among the four types of basic shapes, as a feature value FV2. Then, the feature value FV2 calculated as described above enables, for example, existence or non-existence of a high-grade lesion to be quantitatively determined according to variations in feature value FV2.

Note that the above-described feature value FV2 calculation methods can be employed in a substantially same manner whether a part or all of image regions in one image data is subject to the calculation.

Note that for example, before calculation of a feature value FV1 or FV2 using any of the above-described calculation methods, the feature value calculating section 34 in the present embodiment may perform threshold value processing based on at least one measurement value from among the width, the length and the area of each structural object extracted in step S12 in FIG. 4 to calculate the feature value FV1 or FV2 only for a structural object having the measurement value meeting a predetermined condition.

More specifically, the feature value calculating section 34 in the present embodiment may be, for example, one that performs processing for calculating a feature value FV1 (FV2) only for, from among respective structural objects each including a region including a group of pixels matched with the circle basic shape, a structural object including such region having an area equal to or below a threshold value TH1.

Also, the feature value calculating section 34 in the present embodiment may be, for example, one that performs processing for calculating a feature value FV1 (FV2) only for, from among respective structural objects each including a region including a group of pixels matched with the straight line basic shape, a structural object including such region having a width that is equal to or exceeds a threshold value TH2 and is below a threshold value TH3.

Then, as a result of the threshold value processing being performed before the processing relating to feature value FV1 (FV2) calculation, for example, a structural object that is not suitable for feature value FV1 (FV2) calculation can be excluded from the respective structural objects labeled by the labeling processing section 33, and as a result, an accuracy of feature value FV1 (FV2) calculation result can be enhanced.

Note that the feature value calculating section 34 in the present embodiment is not limited to one that obtains a result of calculation of either a feature value FV1 or FV2 in the processing in step S4 in FIG. 3, and may obtain both results of calculation of feature values FV1 and FV2.

The structural object classifying section 35 classifies the respective structural objects labeled by the labeling processing section 33, based on the feature values obtained as results of processing in step S4 in FIG. 3 (step S5 in FIG. 3).

More specifically, for example, where a frequency of appearance of pixels matched with each of the four types of basic shapes (corresponding to the feature value FV1) is calculated for each structural object, the structural object classifying section 35 classifies a structural object whose frequency of appearance of pixels matched with the straight line basic shape is highest into straight line shape blood vessels. Also, for example, where a frequency of appearance of pixels matched with each of the four types of basic shapes (corresponding to the feature value FV1) is calculated for each structural object, the structural object classifying section 35 classifies a structural object whose frequency of appearance of pixels matched with the divarication basic shape is highest into non-straight line shape blood vessels.

Note that the structural object classifying section 35 in the present embodiment may be one that classifies each structural object in the processing in step S5 in FIG. 3, for example, based on a result of determination of which type, from among a plurality of types (classification patterns) for which the feature values obtained in step S4 in FIG. 3 are set in advance, the structural object is closest to.

Also, the structural object classifying section 35 in the present embodiment may be one that classifies each structural object in the processing in step S5 in FIG. 3, for example, based on a result of clustering being performed using the feature value calculation result obtained in step S4 in FIG. 3.

Also, the structural object classifying section 35 may be one that classifies each structural object in the processing in step S5 in FIG. 3 using other information that is different from the feature values obtained in step S4 in FIG. 3. More specifically, the structural object classifying section 35 may be one that in the processing in step S5 in FIG. 3, for example, scans each region subsequent to region division, obtains information indicating adjacency relationships among the regions of the respective basic shapes obtained based on results of the scan in the form of a tree structure for each structural object, compare the obtained tree structure and a tree structure described in a predetermined template, with each other and classifies each structural object based on a result of the comparison.

FIG. 10 is a diagram illustrating an example of a case where basic shapes included in the region AR1 in FIG. 7 are represented in the form of a tree structure.

Here, the structural object classifying section 35 in the present embodiment, for example, scans the region AR1 in FIG. 7 from the left side to the right side of the image data, and if a result of the scan is represented in the form of a tree structure, can obtain information including the tree structure TAR1 in FIG. 10.

Also, the feature value calculating section 34 in the present embodiment may be one that calculates a feature value FA according to a relationship between a plurality of structural objects based on a result of classification of each structural object obtained in the processing in step S5 in FIG. 3.

More specifically, the feature value calculating section 34 in the present embodiment may be one that calculates, for example, a frequency of appearance of structural objects classified into straight line shape blood vessels and a frequency of appearance of structural objects classified into non-straight line shape blood vessels where all structural objects included in an arbitrary image region in image data is 100%, as a feature value FA.

Then, as a result of processing using the feature value FA being further performed, for example, a property of a living body mucous membrane included in an image region for which the feature value FA has been calculated and/or a site in a body cavity corresponding to the image region can be identified.

Also, as a result of processing using the feature value FA being further performed, for example, whether or not a plurality of structural objects included in an image region for which the feature value FA has been calculated have a peculiar arrangement and/or whether or not a plurality of structural objects classified into a particular type exist densely can be determined.

According to the above-described processing in the present embodiment, each pixel or each region included in an arbitrary structural object in an image (image data) to be processed is matched with any of basic shapes, and feature values are calculated based on a result of the matching. Therefore, according to the above-described processing in the present embodiment, even where a structural object in a living body tissue included in an image (image data) to be processed has a shape including a complicated pattern, the pattern can easily be quantified.

Note that the present invention is not limited to each of the embodiments described above, and it should be understood that various alterations and applications are possible without departing from the spirit of the invention.

What is claimed is:

1. An image processing apparatus comprising:
a basic shape matching section that extracts, as a structure region, a predetermined structural object in an image obtained by picking up an image of a mucosal surface of a living body, the image including at least one pixel, and matches each of regions resulting from the structure region being divided, the regions each including at least one pixel, with a first region having a first basic shape or a second region having a second basic shape that is different from the first basic shape;
a feature value calculating section that sequentially sets regions of interest from among the regions matched by the basic shape matching section, and calculates counts of the first regions and the second regions adjacent to each of the sequentially set regions of interest; and
a classification section that classifies the structure region based on a result of the calculation by the feature value calculating section.

2. The image processing apparatus according to claim 1, wherein the first basic shape is any one of four shapes that are a circle, a straight line, a curve and a divarication, and the second basic shape is any one of the four shapes that is different from the first basic shape.

3. The image processing apparatus according to claim 1, wherein the classification section classifies the structure region into either a straight line shape structural object or a non-straight line shape structural object based on a result of the calculation by the feature value calculating section.

4. The image processing apparatus according to claim 1, wherein the classification section determines a classification pattern that is most similar to the structure region from among a plurality of classification patterns set in advance, based on a result of the calculation by the feature value calculating section, and classifies the structure region based on a result of the determination.

5. The image processing apparatus according to claim 1, wherein the classification section performs clustering using a result of the calculation by the feature value calculating section, and classifies the structure region based on a result of the clustering.

6. The image processing apparatus according to claim 1, wherein the feature value calculating section sequentially sets the regions of interest only for a structural object having a measurement value of at least one of a width, a length and an area, the measurement value meeting a predetermined condition, from among respective structural objects extracted by the basic shape matching section.

7. A method for operation of an image processing apparatus, the method comprising:
- a basic shape matching step of a basic shape matching section extracting, as a structure region, a predetermined structural object in an image obtained by picking up an image of a mucosal surface of a living body, the image including at least one pixel, and matching each of regions resulting from the structure region being divided, the regions each including at least one pixel, with a first region having a first basic shape or a second region having a second basic shape that is different from the first basic shape;
- a feature value calculating step of a feature value calculating section setting regions of interest from among the regions matched in the basic shape matching step, and calculating counts of the first regions and the second regions adjacent to each of the set regions of interest; and
- a classification step of a classification section classifying the structure region based on a result of the calculation in the feature value calculating step.

8. The method for operation of an image processing apparatus according to claim 7, wherein the first basic shape is any one of four shapes that are a circle, a straight line, a curve and a divarication, and the second basic shape is any one of the four shapes that is different from the first basic shape.

9. The method for operation of an image processing apparatus according to claim 7, wherein the classification step includes classifying the structure region into either a straight line shape structural object or a non-straight line shape structural object based on a result of the calculation in the feature value calculating step.

10. The method for operation of an image processing apparatus according to claim 7, wherein the classification step includes determining a classification pattern that is most similar to the structure region from among a plurality of classification patterns set in advance, based on a result of the calculation in the feature value calculating step, and classifies the structure region based on a result of the determination.

11. The method for operation of an image processing apparatus according to claim 7, wherein the classification step includes performing clustering using a result of the calculation in the feature value calculating step, and classifying the structure region based on a result of the clustering.

12. The method for operation of an image processing apparatus according to claim 7, wherein the feature value calculating step sequentially sets the regions of interest only for a structural object having a measurement value of at least one of a width, a length and an area, the measurement value meeting a predetermined condition, from among respective structural objects extracted in the basic shape matching step.

* * * * *